(12) United States Patent
Andjelic et al.

(10) Patent No.: US 12,156,650 B2
(45) Date of Patent: Dec. 3, 2024

(54) ADAPTIVE SUTURES DYNAMICALLY CHANGING WOUND HOLDING PROPERTIES POST-IMPLANTATION

(71) Applicant: Ethicon, Inc., Somerville, NJ (US)

(72) Inventors: Sasa Andjelic, Nanuet, NY (US); Marc Wisnudel, Millburn, NJ (US); Kenneth M. Keilman, Somerville, NJ (US); Leo B. Kriksunov, Ithaca, NY (US); Robert J. Tannhauser, Bridgewater, NJ (US)

(73) Assignee: Ethicon, Inc., Raritan, NJ (US)

( * ) Notice: Subject to any disclaimer, the term of this patent is extended or adjusted under 35 U.S.C. 154(b) by 405 days.

(21) Appl. No.: 17/546,386

(22) Filed: Dec. 9, 2021

(65) Prior Publication Data

US 2022/0192662 A1    Jun. 23, 2022

Related U.S. Application Data

(60) Provisional application No. 63/128,598, filed on Dec. 21, 2020.

(51) Int. Cl.
*A61B 17/06* (2006.01)
*A61L 17/04* (2006.01)
(Continued)

(52) U.S. Cl.
CPC ........ *A61B 17/06166* (2013.01); *A61L 17/04* (2013.01); *A61L 17/12* (2013.01);
(Continued)

(58) Field of Classification Search
CPC ...... A61F 2250/0007; A61F 2250/0004; A61F 2250/001; A61F 2250/0012; A61L 17/04;
(Continued)

(56) References Cited

U.S. PATENT DOCUMENTS

| | | |
|---|---|---|
| 4,621,638 A | 11/1986 | Silvestrini |
| 4,880,002 A | 11/1989 | MacGregor |

(Continued)

FOREIGN PATENT DOCUMENTS

| | | |
|---|---|---|
| EP | 1501559 B1 | 6/2007 |
| WO | 2005065412 A2 | 7/2005 |

(Continued)

OTHER PUBLICATIONS

Bronzino, et al., "Biomedical Engineering Fundamentals", Edition II, Feb. 26, 2018, 8 pages.

(Continued)

*Primary Examiner* — Katherine M Shi
(74) *Attorney, Agent, or Firm* — David R. Crichton; Leo Kriksunov

(57) ABSTRACT

The present invention is directed to a length adaptive surgical suture comprising a monofilament or a braid of a plurality of filaments, the suture having an original length when implanted and a second length that is different from the original length within a first twenty-four (24) hour period of time after implantation to accommodate tissue swelling. The present invention is also directed to configurations and combinations that enable length adaptive results.

10 Claims, 10 Drawing Sheets

(51) Int. Cl.
*A61L 17/12* (2006.01)
*A61B 17/00* (2006.01)

(52) U.S. Cl.
CPC .............. *A61B 2017/00004* (2013.01); *A61B 2017/00951* (2013.01)

(58) Field of Classification Search
CPC .......... A61L 17/00; A61L 17/06; A61L 17/08; A61L 17/10; A61L 17/105; A61L 17/12; A61L 17/14; A61L 17/145; A61L 17/005; A61B 17/06166; A61B 2017/06171; A61B 2017/06176; A61B 2017/0618; A61B 2017/06185; A61B 2017/0619; A61B 2017/00004; A61B 17/0401; A61B 2017/00951; A61B 17/00234; A61B 17/0469

See application file for complete search history.

(56) References Cited

U.S. PATENT DOCUMENTS

| | | | |
|---|---|---|---|
| 4,942,089 A | | 7/1990 | Genba et al. |
| 5,133,739 A | | 7/1992 | Bezwada et al. |
| 5,464,424 A | * | 11/1995 | O'Donnell, Jr. ............................ A61B 17/06166 606/228 |
| 6,162,962 A | | 12/2000 | Hinsch et al. |
| 6,712,838 B2 | | 3/2004 | D, Aversa et al. |
| 6,966,918 B1 | | 11/2005 | Schuldt-hempe et al. |
| 7,913,365 B2 | | 3/2011 | Genova et al. |
| 8,088,146 B2 | | 1/2012 | Wert et al. |
| 8,216,497 B2 | | 7/2012 | Lindh, Sr. et al. |
| 8,870,915 B2 | | 10/2014 | Mayer et al. |
| 2004/0167546 A1 | * | 8/2004 | Saadat ............. A61B 17/00234 606/144 |
| 2005/0177181 A1 | * | 8/2005 | Kagan ................... A61F 5/0076 606/151 |
| 2006/0121274 A1 | | 6/2006 | Capurro |
| 2009/0299408 A1 | * | 12/2009 | Schuldt-Hempe ..... D04B 21/20 606/230 |
| 2015/0073474 A1 | * | 3/2015 | Hodgkinson .... A61B 17/06166 606/228 |
| 2018/0092736 A1 | * | 4/2018 | Lee .................. A61B 17/06066 |
| 2023/0398257 A1 | * | 12/2023 | Maehara ............... A61L 17/105 |

FOREIGN PATENT DOCUMENTS

| | | |
|---|---|---|
| WO | 2015134763 A1 | 9/2015 |
| WO | 2022137003 A1 | 6/2022 |

OTHER PUBLICATIONS

Chu, et al., "Wound Closure Biomaterials and Devices", edited by J. Anthony von, 1997, 413 pages.
De Santis, et al., "Analysis of Shrinkage Development of a Semicrystalline Polymer during Injection Molding", Ind. Eng. Chem. Res. 2010, vol. 49, pp. 2469-2476.
Invitation to Pay Additional Fees received for Application No. PCT/IB2021/061522, mailed on Mar. 11, 2022, 12 pages.
Bronzino, J.D. and Peterson, D.R., "The Biomedical Engineering Handbook", Four Volume Set (4th ed.), CRC Press, 2015, 2 pages.
Joyce Y. Wong, et al., "Biomaterials: Principles and Practices", 2007, 294 pages.
Martin W King, et al., "Biotextiles as Medical Implants", Wood Head Publishing Ltd., 2013, 10 pages.
P Vadgama, "Surfaces and Interfaces for Biomaterials", 2005, 9 pages.
Yixiang Dong, et al., "Degradation Behaviors of Electrospun Resorbable Polyester Nanofibers", Tissue Engg. Part B, 2009, vol. 5(3), pp. 333-351.

* cited by examiner

FIG 4D.

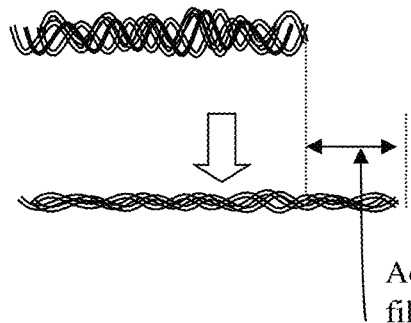

One tight filament/yarn holding braid with braid loosening up upon dissolution

Added length upon dissolution of tight filament

FIG 4E.

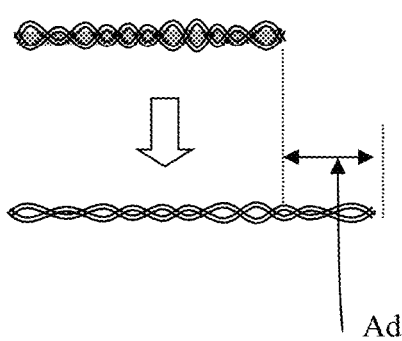

Tight braid held by adhesive with braid loosening up upon adhesive dissolution

Added length upon dissolution of adhesive

FIG 4F.

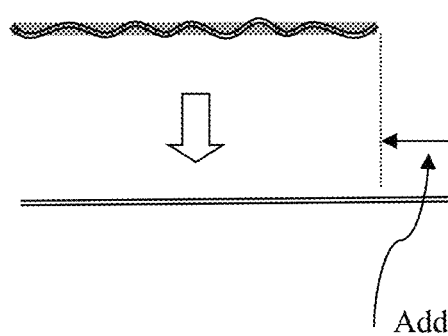

Monofilament or braid held by adhesive in a wavy configuration, with construct loosening up and elongating upon adhesive dissolution Added length upon dissolution of adhesive

ADAPTIVE SUTURES DYNAMICALLY CHANGING WOUND HOLDING PROPERTIES POST-IMPLANTATION

TECHNICAL FIELD

The field of art to which this invention relates is sutures capable of adapting to the changing wound and tissue environment including elongating and or shrinking in a human body post-implantation to respond and adapt to increase and decrease in tissue swelling or to tighten certain body tissues or as healing progresses.

BACKGROUND OF THE INVENTION

Surgical sutures and attached surgical needles are well known in the art for use in a variety of conventional surgical procedures. For example, such sutures may be used to approximate tissue about incisions or lacerations in epidermal layers and underlying fascia layers, join blood vessel ends, attach tissue to medical devices such as heart valves, repair body organs, repair connective tissue, etc. Conventional surgical sutures may be made from known biocompatible materials, particularly synthetic and natural biocompatible polymeric materials, which may be non-absorbable or absorbable. Examples of synthetic non-absorbable polymeric materials useful to manufacture non-absorbable sutures include polyesters, polyolefins, polyvinylidene fluorides and polyamides, polypropylene, nylon, etc. Examples of synthetic absorbable polymeric materials useful to manufacture absorbable sutures include polymers and copolymers made from lactones such as the lactides, glycolide, p-dioxanone, ε-caprolactone, and trimethylene carbonate. The term absorbable is meant to be a generic term, which may also include bioabsorbable, resorbable, bioresorbable, degradable or biodegradable.

Both absorbable and non-absorbable sutures must be capable of providing the desired tensile strength in vivo for a sufficient period of time to allow for effective tissue healing. Wound healing is dependent on the nature of the specific tissue as well as the healing characteristics of the individual undergoing the surgical procedure. For example, there are some instances where tissues and organs swell rapidly after surgical procedures or some mechanical injuries. Closing the wound edges after completing the invasive procedures hold edges well, but after a certain period of time swelling start to decrease. This process could make makes conventional sutures loose, since the regular sutures cannot adapt to this new tissue shrinking tendency. Further, tissue healing can also result in further shrinkage of the tissue. This can, in turn, produce undesired leakages and wound openings.

In view of the swelling of tissues after the suturing there is a strong need to create an adaptive/dynamic tissue-specific suture that will close the wound in a regular fashion, but adapts to swelling of the tissue, including expanding to accommodate the swelling and/or shrinking back after the swelling subsides. There are also other areas of tissue repair, where shrinking of repair sutures over time can be useful to accommodate tissue healing and subsiding of the swelling. One such area is tendon fixation, where lengthwise shrinkage of 2-3% to 20-30% can be of interest if happens over a few days/weeks.

U.S. Pat. No. 4,942,089, "Rapidly Shrinking Fiber And Water-Absorbing Shrinkable Yarn And Other Materials Comprising Same" discloses a polyvinyl alcohol fiber capable of rapidly shrinking in the presence of water but hardly soluble in water, said fiber being characterized in that the maximum shrinkage percentage in water at 20° C. is not less than 30%, with the time required for the shrinkage percentage to reach 30% being not longer than 10 seconds, that the shrinkage stress in water at 20° C. as measured in the original length state is not less than 150 mg/dr, with the time required for the shrinkage stress of 150 mg/dr to appear being not longer than 10 seconds, that the shrinkage stress in water at 20° C. as measured in the state of 30% shrinkage relative to the original length is not less than 30 mg/dr and that the weight loss due to dissolution upon dispersion in water at 200° C. is not more than 45%.

DYNACORD™ Suture manufactured by DePuy Synthes is designed to expand radially and contract axially when laxity is present to allow the suture to minimize negative aspects of a repair such as suture laxity, creep, and knot slippage. DYNACORD™ Suture is a high-strength orthopedic suture that is designed to minimize repair laxity in order to preserve consistent tissue approximation while improving footprint compression. DYNACORD™ Suture is designed to shorten when compression is lost, thereby minimizing micro-motion and gap formation.

U.S. Pat. No. 8,870,915, "Joining Element", discloses a joining element elongate along a longitudinal direction, the joining element comprising: a first material comprising a plurality of threads, the first material elongate along the longitudinal direction; and a second material that extends through the first material along the longitudinal direction, the second material having a volume capable of swelling along a direction transverse to the longitudinal direction, which in turn results in a longitudinal contraction against the first material.

An article titled "Degradation Behaviors of Electrospun Resorbable Polyester Nanofibers", by Yixiang Dong et al., Tissue Eng Part B, 2009 September; 15(3):333-51, discloses Amorphous PLGA or PDLLA electrospun nanofibers shrink during the degradation process because of the thermally induced relaxation of stretched amorphous chains.

An article titled "Analysis of Shrinkage Development of a Semicrystalline Polymer during Injection Molding", by Felice De Santis et al., *Ind. Eng. Chem. Res.* 2010, 49, 2469-2476, discloses a study of shrinkage in injection molding of a semicrystalline polymer and the effect of the holding time and pressure on the shrinkage evolution from the instant of first solidification inside the mold to just after molding.

U.S. Pat. No. 8,088,146 "High-Strength Suture", discloses a surgical suture comprising an elongate woven braid of fibers corresponding to a size within a range of USP size 5-0 to USP size 7 suture, said braid having 8 to 32 fibers braided together at about 50 to about 70 picks per inch, greater than 90% of said fibers of said braid being ultra-high molecular weight polyethylene fiber, said braid of fibers being hollow and defining an elongate, longitudinally-extending, open central chamber without a core material extending therein, said chamber having a cross-sectional diameter that is substantially larger than a diameter of the fibers and said chamber enabling a cross sectional shape of said braid to change in response to pressures experienced when the suture is knotted to permit the formation of knots that resist slippage, and wherein said suture has a diameter in the range from 0.100 mm to 0.999 mm, and wherein said suture has a substantially circular round cross-sectional configuration which collapses in response to pressures experienced when the suture is knotted, and wherein a total denier of said suture is between about 880 to 3520 denier.

U.S. Pat. No. 4,880,002, "Stretchable Porous Sutures", discloses a non-braided surgical suture, comprising: a suture material including: an elongated flexible, non-metallic generally cylindrical member having a plurality of pores, said porous elongated flexible member being elastomeric and being a generally cylindrical and flexible extrudate of a mixture of polymeric material and elutable material, said extrudate having been subjected to elution of said elutable material from said polymeric material to thereby form said pores of the porous elongated flexible and elastomeric member, said polymeric material being selected from the group consisting of polyurethanes and polycarbonates; said elongated flexible and elastomeric member has an initially extruded length and is axially stretchable up to about twice its said initially extruded length or more, whereby said suture is compliant with host tissue when it is implanted; and said elongated flexible and elastomeric member has an external diameter that is no larger than that of a surgical suture and a porous surface that promotes a tissue ingrowth into said porous elongated flexible member.

U.S. Patent Application Publication No. 2006/0121274, "Sheathed Elastic Surgical Thread", discloses surgical thread, wherein it has an elastic core and a non-elastic sheathing, in which the elastic core consists of one or more bio-compatible elastic threads, and the sheathing consists of one or more non-stretch threads made of bio-compatible material and wherein the non-stretch sheathing thread or threads and the elastic core are made of non-absorbable material, and wherein the non-stretch sheathing thread is wound in a spiral fashion, forming one or more overlying spirals wound in opposite directions, with the windings to limit the maximum extension of the elastic thread.

European Patent Publication EP1501559 B1, "Surgical Thread And Surgical Implant With The Same", discloses a surgical thread comprising a core that is made from at least one resorbable material and a covering that is made from at least one non-resorbable material and/or slowly resorbable material which is more slowly resorbable than the resorbable material of the core, the covering comprising threads and characterized in that the threads of the covering are arranged in the surgical thread as a single covered twist or a spinning covering twist and wherein before the resorption of the core, the threads of the covering are dimensionally stabilized against tensile forces by the core, and wherein after resorption of the core, the dimensional stabilization is missing so that when subjected to a tensile force, the covering can move from its non-linear arrangement into a thereabouts linear arrangement. The reference discloses very large elongations that are achieved at times that are much longer than tissue swelling time frames and thus will be excessive for accommodating tissue swelling.

U.S. Pat. No. 6,966,918, "Reinforced Areal Implant" discloses a reinforced areal implant, comprising a net-type basic structure having a pore size in the mange of 1.5 mm to 4.0 mm and textile strengthening elements whose bending resistance, measured in a three-point flexibility test at a support length of 20 mm, is in the range of 0.015 N/mm to 0.4 N/mm, where the textile strengthening elements form a net-type strengthening structure with a pore size in the range of 5 mm to 30 mm, said pore size being a multiple of the pore size of the basic structure.

U.S. Pat. No. 6,162,962, "Areal Implant" discloses an areal implant comprising: a flexible knitted fabric having an initial tearing strength which optionally has a resorption time of at least 60 days, wherein the flexible knitted fabric is designed to stretch more than a tissue region destined to receive the implant below a critical force and stretch less than the tissue region above the critical force, the critical force being below a highest load allowable for this tissue region, and a synthetic resorbable material, which stiffens the flexible knitted fabric, whose resorption time is less than that of the flexible knitted fabric, wherein the synthetic resorbable material is elected from the group consisting of yarns, monofilaments, and combinations thereof.

There is a need in dynamic or adaptive sutures that are designed to accommodate tissue swelling and or tissue shrinkage immediately after the surgical procedure, i.e. sutures that configured to expand (elongate) and contract (shrink lengthwise) after surgery to accommodate tissue responses and healing.

SUMMARY OF THE INVENTION

Briefly, an adaptive or dynamic surgical suture is configured to dynamically change wound holding properties (suture length) post-implantation. In one embodiment, after implantation and exposure to tissue and body fluids, the inventive suture decreases its length, or shortens, or shrinks lengthwise, thus tightening the wound or tissue holding as tissue heals and tissue swelling subsides. In another embodiment, after implantation and exposure to tissue and body fluids, the inventive suture first elongates or extends lengthwise, thus accommodating the tissue swelling, and thereafter suture permanently decreases its length or shrinks lengthwise, thus tightening wound or tissue holding as tissue heals and tissue swelling subsides.

In some embodiments, the inventive suture can be a monofilament or braided suture, absorbable or non-absorbable suture, and is used to close the wound or to connect tissues during surgical repair in an established way as it is known in the surgical arts. The suture then optionally extends lengthwise or elongates upon exposure to the body fluids and tissues to help release tension as tissue swells post-surgery. In some embodiments, the inventive suture optionally elongates 2, 3, 5, 7, 10, 15, 20% of the original length, most preferably about 10%, within 2, 4, 6, 12, 18, 24, 30, 36, 48 hours after suture installation, preferably within about 18-36 hours, most preferably within about 24 hours.

After the elongation step, which can be optional, the inventive suture shortens lengthwise, or shrinks, to accommodate the subsiding of tissue swelling and tissue healing process. In some embodiments, the inventive suture shrinks to reach between about 75% and 100% of the original length, more preferably between about 80 and 98%, most preferably between about 90% to 95% of the original length, within between about 36 and 96 hours after surgery, more preferably within between about 48 to 72 hours.

In some embodiments, rapid dissolution of certain sacrificial yarns or elements in the suture construct causes suture to relax and elongate and thus to accommodate swelling of tissue. Later crystallization of amorphous or semi-amorphous suture material causes suture to contract, tightening up after swelling subsides or healing progresses.

In one embodiment, the present invention is directed to a length adaptive surgical suture comprising a monofilament or a braid of a plurality of filaments, the suture having an original length when implanted and a second length that is different from the original length within a first twenty-four (24) hour period of time after implantation to accommodate tissue swelling. The suture can be in the form of a monofilament or at least one filament in the braid of a plurality of filaments have a plurality of releasable loops that are retained in position by an adhesive that dissolves in the presence of physiologic fluid or a biocompatible solvent.

Alternatively, the suture can be a plurality of filaments held by a constricting yarn in a constricted state as an original length that is shorter than the second length, wherein such constricting yarn rapidly dissolves upon exposure to body fluids and tissue. In further alternative, the suture can be in the form of a plurality of filaments arranged in a braid, with a constricting yarn forming a core of the braid and holding the braid in a constricted shortened state, wherein said constricting yarn is rapidly dissolves upon exposure to body fluids. In another alternative, the suture can be in the form of a plurality of filaments arranged in a braid, held in a tight shortened configuration by a biocompatible soluble adhesive. In a still further alternative, the suture can be in the form of at least one filament held by a biocompatible soluble adhesive or coating in a wavy configuration as an original length.

The present invention is also directed to length adaptive surgical sutures comprising a monofilament or a braid of a plurality of filaments, the suture having an original length when implanted and a second length that is shorter from the original length. The shortening suture embodiment can be in the form of a monofilament or a braid of a plurality of filaments. In one aspect of the shortening suture, the second length is at least 10% less than the original length within the first twenty-four (24) hour period post-implantation.

In some embodiments, each filament has a diameter that increases between 5% and 10% in a body post-implantation.

In at least one embodiment, at least some of the filaments in the suture are extruded from a semi-crystalline polymer having a glass transition temperature between 40° C. and 55° C. and exhibit a crystallinity level between 10% and 25%.

Each embodiment of adaptive sutures can be made from one or more filaments of an absorbable polymer or a non-absorbable polymer or blends thereof. Additionally, the monofilament or each filament in the plurality of braids can have a suture tensile strength and a knot strength that each increase by at least about 20% in a body post-implantation prior to a major degradation and hydrolysis of said suture.

The present invention is directed to an adaptive surgical suture comprising a semi-crystalline absorbable synthetic polymer made from glycolide and lactide copolymer having an original length, a glass transition temperature in between 40° C. and 45° C. and a crystallinity level of about 15%, wherein said suture has a second length that decreases about 15% post-implantation and a diameter that increases about 10% in a body post-implantation and wherein said suture tensile strength and knot strength increase by at least about 40% in a body post-implantation prior to a major degradation and hydrolysis of said suture.

The present invention is directed to a length adaptive surgical suture comprising a monofilament or a braid of a plurality of filaments, the suture having an original length when implanted and a second length that is greater within the first twenty-four (24) hour period after implantation to accommodate tissue swelling, and a third length thereafter that is less than the original length to tighten the tissue holding as tissue heals.

The suture of the present invention can be provided with at least one elongated filament held by a rapidly soluble constricting element in a shortened or constricted configuration, or wherein elongating of the suture is caused by a rapid dissolution of the constricting element that causes the elongated filament to relax and elongate, or wherein the at least one elongated filament comprises a semi-crystalline polymer having glass transition temperature in between 40° C. and 55° C. and exhibiting a crystallinity level between 10% and 25%, wherein a crystallization of said semi-crystalline polymer causes said suture thereafter to contract, shortening said suture.

BRIEF DESCRIPTION OF THE DRAWINGS

FIGS. 4A, 4B, 4C, 4D, 4E and 4F show embodiments of the present invention related to elongation step

DETAILED DESCRIPTION OF THE INVENTION

Figure 1:
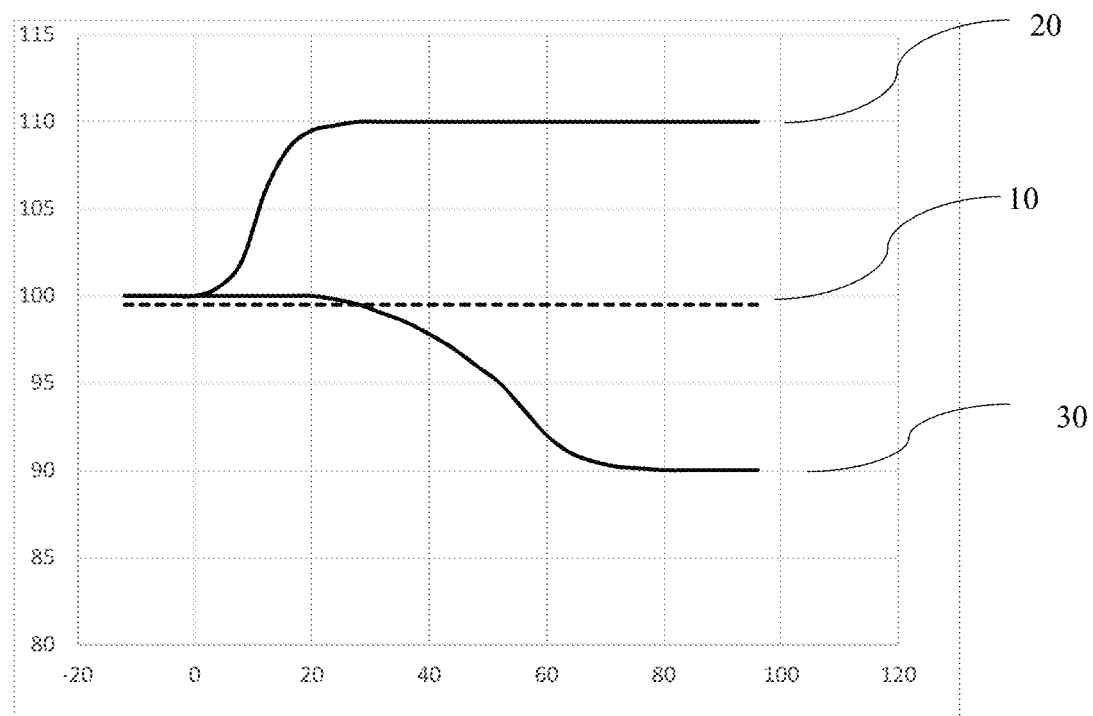
FIGS. 1 and 2 show schematic charts of sutures length post-implantation in percent of the original suture length vs time in hours.
Figure 2:
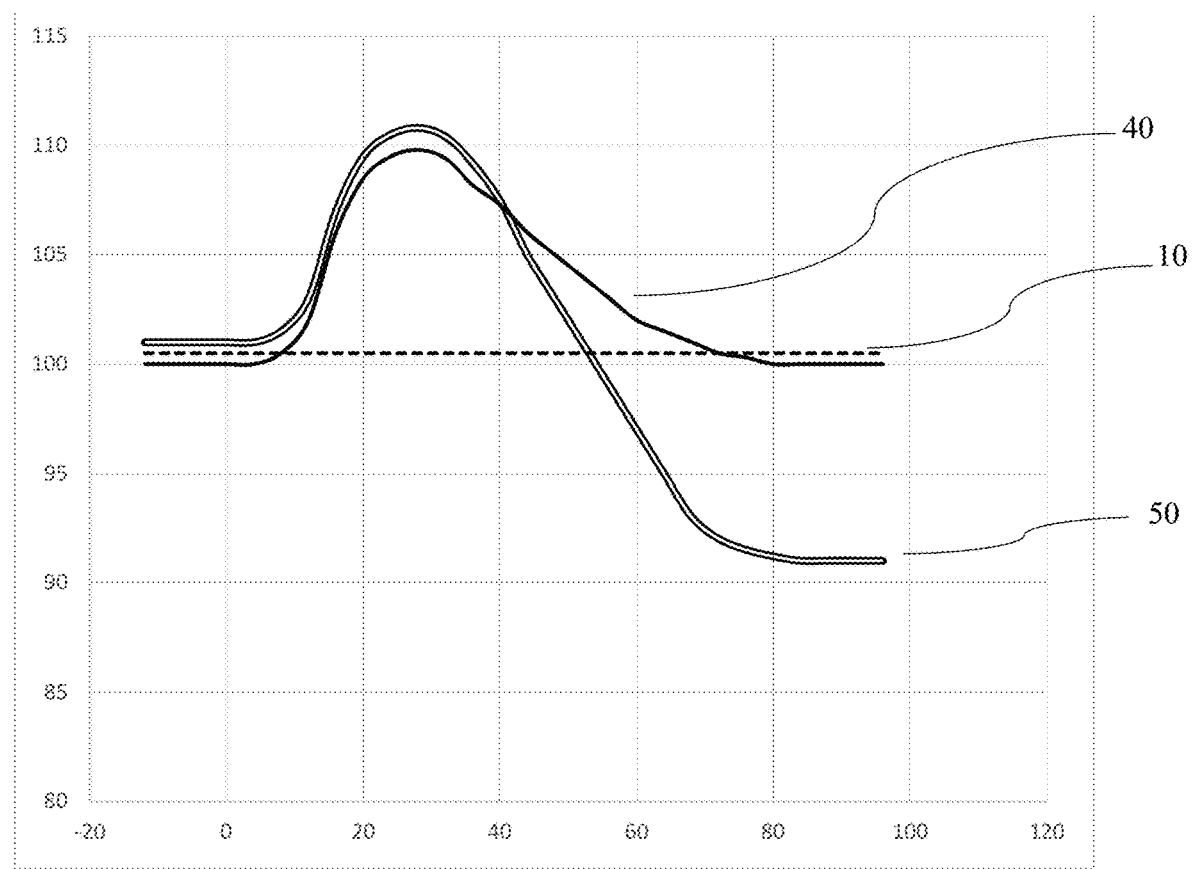

Referring now to FIGS. 1 and 2, schematic charts of sutures length post-implantation in percent of the original suture length are plotted versus time in hours. Zero time represents surgical implantation of the suture and exposure to tissues and body fluids. Dashed line 10 represents customary suture that has no substantial length changes after implantation, i.e. having length of 100% of the starting pre-implantation length throughout the time shown. Line 20 in FIG. 1 shows an embodiment of the inventive suture that provides about 10% elongation starting after installation and completed within about 24 hours. Line 30 in FIG. 1 shows an embodiment of the inventive suture that provides about 10% shrinkage starting after installation and completed within about 80 hours.

Line 40 in FIG. 2 shows an embodiment of the inventive suture that provides about 10% elongation starting after installation, reaching about 110% of the original length within about 24 hours, and then shrinking back to approximately the same length as the original pre-installation length of 100% by about 80 hours.

Line 50 in FIG. 2 shows an embodiment of the inventive suture that provides about 10% elongation starting after installation, reaching about 110% of the original length within about 24 hours, and then shrinking back to approximately 90% of the original pre-installation length by about 80 hours.

Figure 3:
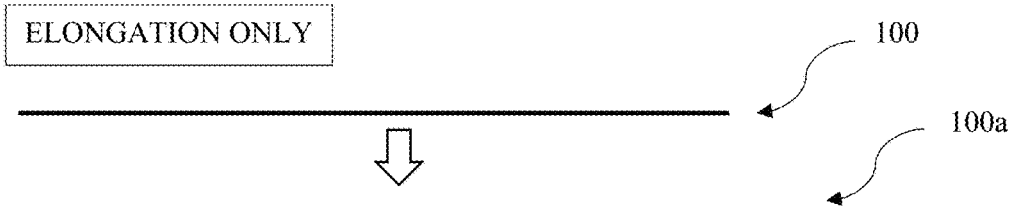
FIG. 3 shows schematic representations of the inventive sutures length after installation.
Figure 3:
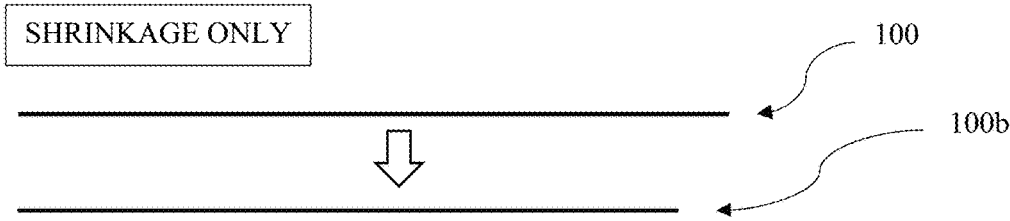
Figure 3:
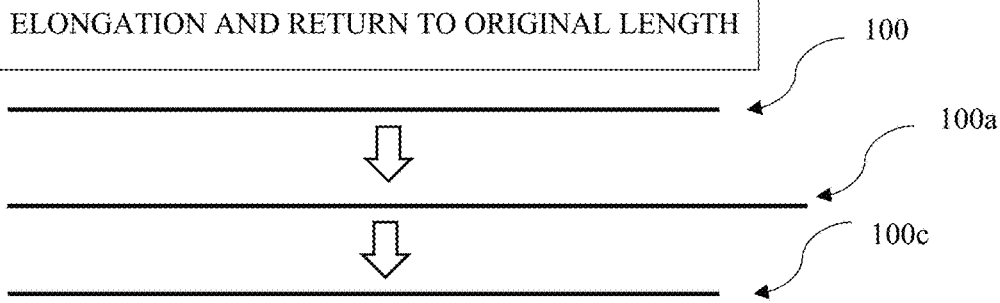
Figure 3:
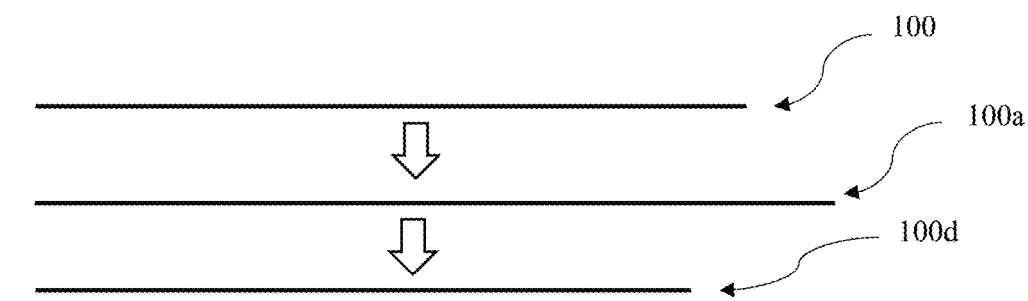

Referring now to FIG. 3, several embodiments of the inventive sutures are schematically shown. In Elongation Only embodiment, corresponding to FIG. 1 line 20, installed suture 100 is shown to elongate after installation to form elongated suture 100a. In Shrinkage Only embodiment, corresponding to FIG. 1 line 30, installed suture 100 is shown to shrink after installation to form shorter suture 100b. In Elongation And Return To Original Length embodiment, corresponding to FIG. 2 line 40, installed suture 100 is shown to elongate after installation to form elongated suture 100a and thereafter is shown to shrink to form suture 100c that has approximately the same length as the original suture 100. In Elongation And Shrinking To Length Shorter Than Original Length embodiment, corresponding to FIG. 2 line 50, installed suture 100 is shown to elongate after installation to form elongated suture 100a and thereafter is shown to shrink to form suture 100d that is shorter than the original suture 100.

In some embodiments, the inventive suture upon installation optionally elongates or extends lengthwise, thus accommodating tissue swelling. The elongation of the suture is enabled by rapid dissolution of components as described below.

Figure 4A:
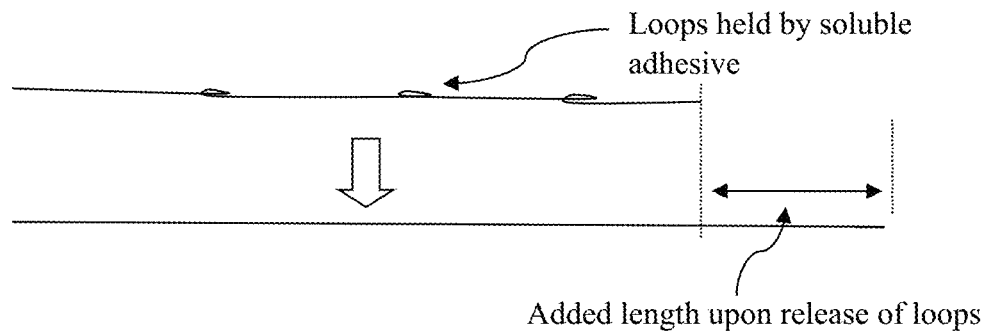

In one embodiment, as shown in FIG. 4A, for a braided or monofilament suture, small suture loops are held by a biocompatible soluble adhesive. Upon exposure to body fluids and tissue, loops are released resulting in elongation of the suture post-installation.

Figure 4B:
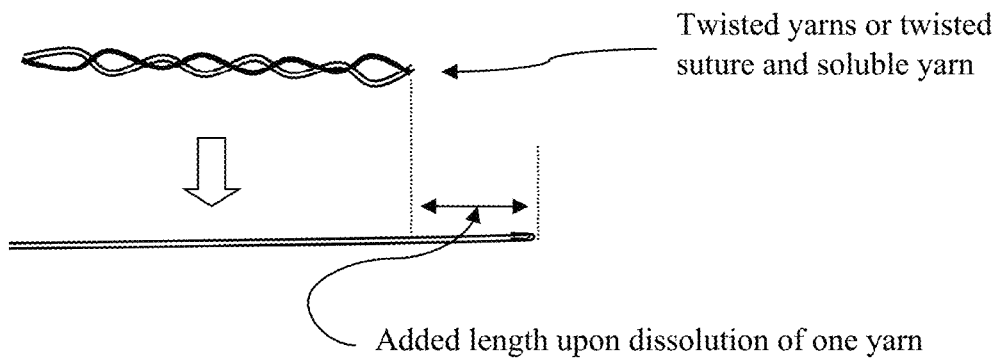

In another embodiment, as shown in FIG. 4B, the inventive suture is formed of a plurality of yarns or filaments twisted together in a unified construct such as braid, with a constricting yarn or filament holding the construct in a constricted or shortened state, such constricting yarn or filament being rapidly soluble or absorbable. Upon exposure to body fluids and tissue, constricting yarn (solid line) is rapidly dissolving and releasing the remaining construct (shown as double line) allowing the suture to extend lengthwise.

Figure 4C:
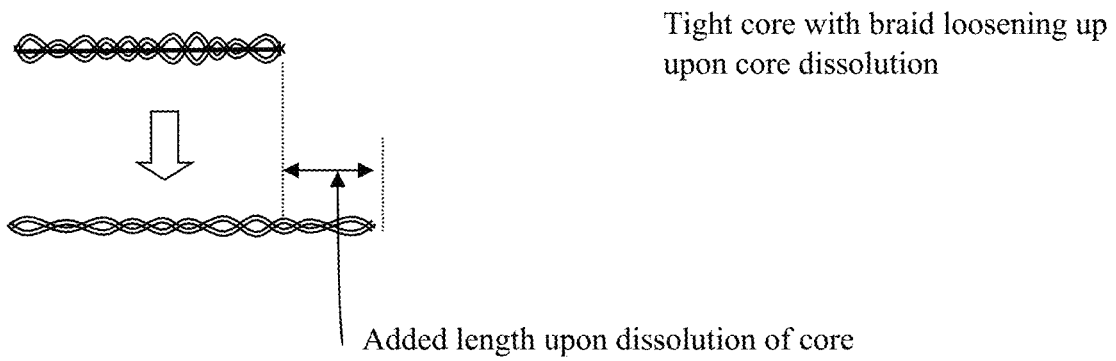

In another embodiment, as shown in FIG. 4C, the inventive suture is formed of a plurality of yarns or filaments forming a unified construct such as braid, with a constricting yarn or filament (solid line) forming the core of the braid and holding the braid in a constricted or shortened state, such constricting core filament being rapidly soluble or absorbable. Upon exposure to body fluids and tissue, constricting filament is rapidly dissolving and releasing the remaining braid construct (shown as double line) allowing the suture to extend lengthwise upon dissolution of core.

In another embodiment, as shown in FIG. 4D, the inventive suture is formed of a plurality of yarns or filaments forming a unified construct such as braid, with a constricting yarn or filament (solid line) forming a part of the braid that is not core of the braid, and holding the braid in a constricted or shortened state, such constricting core filament being rapidly soluble or absorbable. Upon exposure to body fluids and tissue, constricting filament is rapidly dissolving and releasing the remaining braid construct (shown as double line) allowing the suture to extend lengthwise upon dissolution of core.

In another embodiment, as shown in FIG. 4E, the inventive suture is a braid (shown as double line) tightly assembled and held by an adhesive (shown as a semi-transparent solid) in shortened configuration. Upon exposure to body fluids and tissue, adhesive is rapidly dissolving and releasing the remaining braid construct allowing the suture to extend lengthwise.

In another embodiment, as shown in FIG. 4F, the inventive suture is a monofilament or a braid, held by an adhesive (shown as a semi-transparent solid) or adhesive coating in a wavy configuration. Upon exposure to body fluids and tissue, the adhesive rapidly dissolves and releases the construct (shown as double line) allowing the suture to extend lengthwise.

In all embodiments, the rapidly soluble or rapidly absorbable materials are selected to initiate dissolution immediately or within hours after installation into tissue, and complete resorption and/or dissolution within 16 to 48 hours, preferably within 24 hours. Materials include prehydrolyzed polyesters, polyethylene glycol, polyvinyl alcohol, cellulose-based materials, proteins such as albumin, and any biocompatible, rapidly soluble or rapidly bioabsorbable materials.

After the optional elongation step, the inventive suture undergoes shortening, or shrinking, to accommodate the subsiding of tissue swelling or other tissue healing processes. It is to be understood, that shrinkage of the suture will initiate immediately upon exposure to body fluids and tissues, but the effect of the optional elongation will be seen much earlier due to the nature of the elongation process. Thus, while optional suture elongation can be complete within 12 to 24 hours, suture shrinkage may be complete within 48 to 72 hours, or even within 120 or 240 hours.

The homopolymers and copolymers of the present invention can be melt extruded by a variety of conventional means. Monofilament fiber formation can be accomplished by melt extrusion followed by extrudate drawing with or without annealing. Multifilament fiber formation is possible by conventional means. Methods of manufacturing monofilament and multifilament braided sutures are disclosed in U.S. Pat. No. 5,133,739, entitled "Segmented Copolymers of epsilon-Caprolactone and Glycolide" and U.S. Pat. No. 6,712,838 entitled "Braided Suture with Improved Knot Strength and Process to Produce Same", which are incorporated by reference herein in their entirety.

For monofilament suture, in a conventional sense, there is a need for it to be dimensionally stable. Thus, as the molecular orientation of the polymer is increased during fiber processing to increase strength, the driving force to shrink and deform is increased. This is particularly problematic with low glass transition temperature polymers used to make monofilament sutures. Dimensional stability is therefore provided for all conventional suture by virtue of the rapid crystallization of the polymer during fiber formation. General approach in fiber processing step is to prevent highly oriented monofilament suture from shrinking or deforming by generating sufficient level of crystallinity. However, the present invention describes the innovative procedures to provide fibers with only limited amount of crystallinity that will help maintaining dimensional stability of sutures prior the use but change the shape in desired mode when used post-implantation.

Figure 5:
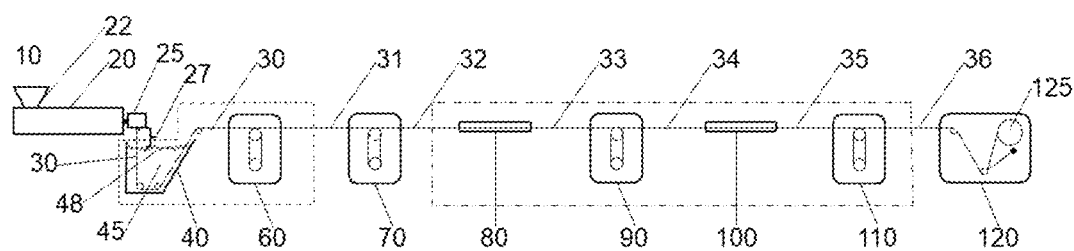
FIG. 5 is a flow diagram of a novel process of the present invention used to produce the novel sutures of the present invention.

An example of the novel monofilament extrusion of the present invention for glycolide and lactide copolymer is diagrammatically illustrated in the flow diagram of FIG. 5. As noted, either absorbable or non-absorbable polymer composition can be used to practice art of this invention. A polymer resin in granular or pellet form 10 useful to manufacture the novel sutures of the present invention is fed into the nitrogen purged hopper 22 of extruder 20. The polymer 10 is then heated, melted and worked by the extruder 20 such that it is in a flowable state. The molten polymer 10 is then discharged from the outlet 25 of the extruder 20 in the form of a monofilament fiber extrudate 30.

The fiber extrudate 30 is pulled into the quench bath 40 containing chilled water 45; although a wide range of quench bath temperatures can be employed, a temperature of 20° C. is particularly preferred. The "air gap" 27, which is the distance between the bottom of extruder outlet 25 and the water surface 48 of the quench bath 40, will typically range from about 0.05 inches to about 2.0 inches. An air gap of about 0.1" to about 0.5" is particularly preferred. The fiber extrudate 30 resides in the water media 45 of the quench bath 40 for a sufficient period of time to effectively provide the required polymer morphology, particularly crystal nucleation, of the polymer chains of fiber extrudate 30. The residence time of the extrudate fiber 30 in the water media 45 of the quench bath 40 is controlled by the line speed of the extrudate fiber 30 and the path length of the extrudate fiber 30 within the water media 45. The residence time of the extrudate fiber 30 in the water media 45 of the quench bath 40 is typically from about 1 second to a few minutes (e.g., about 3 minutes). The level of crystallinity of the fiber 30 after exiting the quench bath 40 needs to be low enough, i.e., sufficiently low, to allow a maximum draw ratio during the subsequent drawing steps of at least 8.0. If the level of crystallinity of the fiber 30 exiting the bath 40 is too high, the fiber breaks if one tries to achieve the higher draw ratio, limiting the molecular orientation and thus the tensile strength of the fiber. The fiber extrudate 30 then moves to the rolls of godet 60 and then to the rolls of godet 70; the relative linear speed of the rolls of godet 70 to godet 60 is greater than or equal to about 5.5. The fiber, 31, undergoing drawing between godet 60 and godet 70 is thus drawn to a ratio of greater than or equal to about 5.5. The godets 60 and 70 may be optionally heated (e.g., from about 30° C. to 90° C.) to allow for smoother drawing.

As shown in FIG. 5, the filament 32 is next moved to the first hot air oven 80 where it is heated to a sufficiently effective temperature (from about 30° C. to 130° C.) for a sufficiently effective residence time in order to provide sufficient crystal growth in fiber 33. The residence time in the hot air oven 80 is controlled by the line speed of the fiber 32/33 and the path length of the fiber within the hot air oven 80. The fiber 32 playing off the rolls of godet 70, in addition to optionally undergoing heat treatment in hot air oven 80, may also undergo further drawing by employing godet 90. The draw ratio between godet 90 and godet 60 will typically be about 6.5 or greater. Optionally, the rolls of godet 90 can be heated (from about 30° C. to 90° C.) to allow for easier drawing. The filament 34 emerging from the rolls of optional godet 90 is then moved to a second hot air oven 100, again heated to a sufficiently effective temperature (from about 30 to 130° C.) for a sufficiently effective residence time in order to achieve optimal polymer morphology resulting in drawn fiber 35. The fiber 34 playing off the rolls of godet 90, in addition to optionally undergoing heat treatment in hot air oven 100, may also undergo further drawing or relaxation by employing godet 110, again resulting in drawn fiber 36. The draw ratio between godet 90 and godet 110 will typically be about 0.8 to about 1.2. The resulting filament 36 is then moved to take up unit 120 where the filament is collected on roll 125. The filament 36 collected on roll 125 can be stored in a nitrogen or vacuum chamber until further use.

During extrusion, a fiber can be drawn without inducing any measurable crystallinity if the polymer's glass transition temperature is above room temperature. Fiber orientation that was achieved during drawing process can be preserved either by having high enough glass transition of the fiber or inducing a specific level of crystallinity to keep morphology intact upon storage.

If desired, the homopolymers and copolymers of the present invention when made into monofilament sutures may be processed to have barbs. Such barbs can be emplaced or incorporated in a conventional manner including cutting, molding, pre-forming, forming, attaching, etc. An example of a barb-forming process is disclosed in the U.S. Pat. No. 8,216,497 "Tissue Holding Devices and Methods for Making the Same" which is incorporated herein by reference. An alternate process of making barbed sutures is a cutting process. An example of a barb-cutting process is disclosed in the U.S. Pat. No. 7,913,365 "Method of Forming Barbs on a Suture and Apparatus for Performing Same".

The monofilament or multifilament sutures of the present invention may contain, if desired, medically useful substances. The medically useful substances may be incorporated into or onto the sutures in a variety of conventional manners including compounding, coating, spraying, dipping, sputtering and the like. The sutures of the present invention may be delivered to the surgeon in a variety of lengths. Preferably, conventional surgical needles are mounted to one end or both ends of the sutures (i.e., single-armed or double-armed), although the sutures may be unarmed with no surgical needles mounted.

The medically useful substances that may be incorporated in the surgical sutures of the present invention include antimicrobials, therapeutic agents, antibiotics, and other components or agents.

The process equipment that can be used in the processes of the present invention will be conventional equipment that is readily commercially available. An example of a monofilament extruder that is useful in the practice of the present invention is a Davis-Standard extruder, model no. 22450, available from Davis-Standard, Cedar Grove, NJ, USA. An example of godets useful in the practice of the present invention is a J J Jenkins godet, Model No. 9397, available from J J Jenkins, Inc., Matthews, NC, USA. An example of a hot air oven useful in the practice of the present invention is a J J Jenkins oven, Model No. 74DM1115-3 available from J J Jenkins, Inc., Matthews, NC, USA. An example of a take-up unit useful in the practice of the present invention is a Georg Sahm take-up unit, Model No. 283 E, manufactured by Georg Sahm GmbH, Eschwege, Germany.

Different characterization methods, described below, were used to measure key properties of the polymer fibers produced to support this application.

Differential Scanning Calorimetry (DSC), tensile and other analytical data were used to fingerprint the produced fiber. The DSC instrument used was a TA Instruments (New Castle, DE USA) Model Q20 equipped with fifty-position robotic autosampler.

Mechanical properties of the fibers before and after hydrolysis treatment, such as straight tensile and knot tensile strength (one simple knot in the middle) were measured by the Instron tester. The Instron model was ID #TJ-41, equipped with 100-lb load cell LC-147 with pneumatic grips at clamping pressure around 60 psi. The Instron Gauge speed was one inch per minute with the Gauge length of one inch. A 100-lb load cell was used. For the time zero, steel faces were used on the Instron machine, for all other hydrolysis times rubber faces were used to avoid slippage. The fiber diameters were measured using Federal gauge (Products Corp. Providence, RI) model #57B-1, identification #W-10761.

In vitro BSR measurements on produced fibers were conducted at physiologically relevant in vitro conditions: 7.27 pH phosphate buffered saline solution with molarity of 0.01 M (1×) maintained at 37° C. temperature. Two Haake water baths equipped with a Thermo Scientific DC10 motor (Model W46, equipment ID: BT-029) were used. The data for BSR evaluations were given in pounds and percentages. At specified time points, the tensile strength of samples was tested using an Instron material testing machine. The test parameters were one inch gauge length and one inch per minute crosshead speed.

The following examples are illustrative of the principles and practice of the present invention, although not limited thereto. Numerous additional embodiments within the scope and spirit of the invention will become apparent to those skilled in the art once having the benefit of this disclosure.

Example 1. Monofilament Extrusion of 90/10 Gly/Lac (PG-910) Copolymer

Monofilament extrusion runs of the 90/10 Gly/Lac (PG-910) random copolymers useful in the practice of the present invention were conducted using a one-inch Davis-Standard Extruder with a 24:1 barrel length (1-22-1 design) equipped with a single grooved feed throat. The die size for each run was 40/1. The random 90/10 Gly/Lac copolymers were processed in accordance with the method described previously herein and illustrated in FIG. 5. A water bath tank capable of heating up to about 50° C., three sets of orientation godets (with heating capability) with one additional relaxation godet at the end of line prior to a collection spool were utilized. Between the second and third godet, and also between the third godet and the final relaxation godet, were two annealing ovens used to heat the fibers to enhance its polymer morphology. The fiber diameter was measured inline using a Mitutoyo Lasermac (laser micrometer) located just before a collection spool.

In this example, for each copolymer run, the bath temperature was set at 20° C., the speed ratios of the godets are listed in Table 1 below. The monofilaments sutures had a suture USP size of 3-0, corresponding to the fiber diameter about 11 mils. Extruder temperature profiles ranged from 205 to 220° C., with die temperature kept at 220° C. for all runs.

TABLE 1

Selected Extrusion Conditions for 90/10 Gly/Lac Size 3-0 Monofilaments

| Sample ID | Godet Speed and Temperature | | | | | | Temp of Hot Air | Temp of Hot Air | Max Draw/Total Draw Ratios |
| --- | --- | --- | --- | --- | --- | --- | --- | --- | --- |
| | G1 | | G2 | | G3 | G4 | Oven One | Oven Two | |
| | fpm | (° C.) | fpm | (° C.) | fpm | fpm | (° C.) | (° C.) | |
| Sample 1-A | 20.0 | 50-75 | 135 | 50 | 150 | 142 | 80 | 80 | 7.50/7.10 |
| Sample 1-B | 27.3 | 50-75 | 145 | 50 | 150 | 147 | 80 | 80 | 5.50/5.38 |
| Sample 1-C | 23.1 | 40-75 | 139 | 50 | 150 | 145 | 80 | 80 | 6.50/6.28 |
| Sample 2 | 23.1 | 40-75 | 139 | 50 | 150 | 145 | 100 | 100 | 6.50/6.28 |
| Sample 3 | 23.1 | 40-70 | 139 | 40 | 150 | 145 | 40 | 40 | 6.50/6.28 |
| Sample 4 | 23.1 | 40-70 | 139 | 40 | 150 | 145 | 60 | 60 | 6.50/6.28 |

The extruded 90/10 Gly/Lac 3-0 monofilaments of the present invention were next collected on spools and stored in a vacuum chamber. Prior to next stage use, the monofilaments were cut into 12 inches pieces.

Example 2. Tensile and Crystallization Properties

Instron tensile properties of fibers produced in Example 1 are given in Table 2.

TABLE 2

Instron Tensile Properties of Drawn 3-0 Monofilaments of Example 1

| Sample* ID | Diameter (mils) | Straight Strength (lbs) | Knot Strength (lbs) | Elongation-to break (%) | Young Modulus (Kpsi) |
|---|---|---|---|---|---|
| Sample 1-A | 11.12 | 7.70 | 1.35 | 14.48 | 1587 |
| Sample 1-B | 11.10 | 6.08 | 4.17 | 30.74 | 1202 |
| Sample 1-C | 11.07 | 7.03 | 2.53 | 21.52 | 1390 |
| Sample 2 | 11.13 | 7.06 | 3.11 | 19.82 | 1518 |
| Sample 3 | 11.21 | 5.62 | 3.48 | 17.60 | 1044 |
| Sample 4 | 11.21 | 6.24 | 4.17 | 18.68 | 1295 |

*the length of each fiber samples was 12.0 inches

In order to estimate crystallization level in fibers presented in Table 1, the first heat DSC measurements, to measure "as is" fiber properties after extrusion, were conducted. The samples were first quenched at a rate of 60° C./min to minus (−)60° C., followed by heating at a rate of 10° C./min to determine their calorimetric properties (first heat properties); these included the glass transition temperature, $T_g$, the crystallization temperature, $T_c$, the heat of crystallization, $\Delta H_c$, the melting point, $T_m$ and the heat of fusion, $\Delta H_m$. Heat of fusion is directly proportional to the level of crystallinity in a sample. If needed, from the second heat measurements (resin was melted at 220° C. and then quenched below −60° C.), values for Tg, Tm, Tc (crystallization temperature), and ΔHm could be obtained that are independent from the previous heat treatment history.

The summary of DSC measurements of the fibers produced in Example 1 on their selected first heat properties is given in Table 3.

Data in Table 3 indicate strong dependency of the hot oven air temperatures on the level of crystallinity developed in the extruded fibers. For instance, the hot oven air temperatures of 80° C. and above, regardless of the draw ratio used (5.5× to 7.5×), produced considerably higher crystallinity levels (above 40%) in 90/10 Gly/Lac fibers than oven temperatures below 80° C. Interestingly, when the temperature of the hot ovens is only 40° C., very low crystallinity (around 7%) seems to be developed in the studied 90/10 Gly/Lac fibers.

It is also important to note that for each fiber run in Table 3, the glass transition temperature was found to be in the range from 41° C. to 47° C. Higher the crystallinity level in fibers (e.g. Samples 1A-C, 2), the higher glass transition was observed. This is because when glycolide moieties crystallize, then amorphous phase, which contributes solely to glass transition temperature, becomes richer in the rigid lactide moieties. This, in turn, raises the overall glass transition temperature of such fibers.

Example 3. Annealing Oven Treatment of Fibers Produced in Example 1

Size 3-0 monofilaments produced in Example 1 were placed in the annealing oven with preset temperature of 37° C. and kept there for several hours or days. After specific time intervals, the sutures were taken out of ovens and examined to see if there is any change in length, diameter, or tensile properties occurred during this "dry" oven exposure. This study will help establishing stability of such suture at ambient conditions up to 37° C.

Summary of data after 37° C. nitrogen oven exposure is presented in Table 4.

TABLE 3

Estimation of Crystallization Properties of Drawn 3-0 Monofilaments of Example 1 by DSC

| Sample ID | Temperatures of Hot Air Ovens One & Two (° C.) | $\Delta H_c$(J/g) | $\Delta H_m$(J/g) | $\Delta H_m$(J/g) − $\Delta H_c$(J/g) | % Crystal.*** | Tg (° C.) |
|---|---|---|---|---|---|---|
| Sample 1-A* | 80 | 6.4 | 54.4 | 48.0 | 46.6 | 46.9 |
| Sample 1-B** | 80 | 4.6 | 53.0 | 48.4 | 47.0 | 44.1 |
| Sample 1-C | 80 | 6.2 | 50.8 | 44.6 | 43.3 | 45.0 |
| Sample 2 | 100 | 4.0 | 54.4 | 50.4 | 48.9 | 44.5 |
| Sample 3 | 40 | 45.1 | 52.7 | 7.6 | 7.3 | 41.8 |
| Sample 4 | 60 | 31.8 | 53.1 | 21.3 | 20.4 | 41.6 |

*Draw ratio for this fiber 7.5x

**Draw ratio 5.5x

***The percent crystallinity was calculated from the heat of fusion of 100% crystalline PGA material ($\Delta H_m$ = 12 KJ/mole, which is equivalent to 103 J/g); [refs.: *Biomedical Engineering Fundamentals* by Joseph D. Bronzino, Donald R. Peterson; *Wound Closure Biomaterials and Devices* edited by Chih-Chang Chu, J. Anthony von; *Biomaterials: Principles and Practices* edited by Joyce Y. Wong, Joseph D. Bronzino, Donald R; *Biotextiles as Medical Implants* edited by M W King, B S Gupta, R Guidoin; *The Biomedical Engineering Handbook 1* by Joseph D. Bronzino; *Surfaces and Interfaces for Biomaterials* edited by P Vadgama]

TABLE 4

Physical and Instron Tensile Properties of Drawn 3-0 Monofilaments of Example 1 After Various Time Exposure in Nitrogen Oven at 37° C.

| Sample* ID | Length (inches) | Diameter (mils) | Straight Strength (lbs) | Knot Strength (lbs) | Elongation-to break (%) | Young Modulus (Kpsi) |
|---|---|---|---|---|---|---|
| Sample 1-A | 11.98 | 11.10 | 7.73 | 1.32 | 14.78 | 1683 |
|  | 11.92 | 11.20 | 7.29 | 1.33 | 13.90 | 1757 |
|  | 11.95 | 11.24 | 7.49 | 1.40 | 14.38 | 1771 |
| Sample 1-B | 12.00 | 11.09 | 6.30 | 3.79 | 31.90 | 1277 |
|  | 11.99 | 11.21 | 6.03 | 3.88 | 31.20 | 1270 |
|  | 11.95 | 11.18 | 6.40 | 3.99 | 30.12 | 1348 |
| Sample 1-C | 11.89 | 11.09 | 6.88 | 2.23 | 21.62 | 1511 |
|  | 11.89 | 11.18 | 7.77 | 2.01 | 23.52 | 1504 |
|  | 11.89 | 11.10 | 7.78 | 2.03 | 23.74 | 1537 |
| Sample 2 | 11.92 | 11.07 | 7.37 | 2.19 | 21.04 | 1538 |
|  | 11.93 | 11.12 | 7.27 | 2.31 | 20.58 | 1570 |
|  | 11.92 | 11.11 | 8.02 | 2.51 | 22.40 | 1591 |
| Sample 3 | 5.00 | 18.43 | NA | NA | NA | NA |
|  | 4.83 | 19.48 | NA, | NA | NA | NA |
|  | 4.23 | 20.13 | NA | NA | NA | NA |
| Sample 4 | 11.58, | 11.40 | 6.21 | 4.19 | 24.40 | 1199 |
|  | 11.10, | 11.82 | 6.61 | 4.08 | 29.78 | 1221 |
|  | 10.74 | 11.85 | 7.14 | 4.04 | 32.20 | 1279 |

*the first numbers in columns represent exposure time of 6 hours, the second numbers exposure time is for 24 hours, and the third numbers exposure time of 120 hours As indicated in Table 4, extreme shrinkage was observed for the amorphous Sample 3 following 6, 24, and 120 hours nitrogen oven exposure at 37° C. The extrudates were found "rolled up and wavy", very difficult to measure length and diameter, and not able to perform Instron testing. Sample 4 shows only a minor change (around 10%) in fiber length and diameter, while other fibers (Sample 1A, 1B, 1C, and 2) showed practically no change in these properties.

Example 4. Breaking Strength Retention, BSR and Physical Properties of Fibers Produced in Example 1 Exposed to Physiological Conditions (37° C./pH=7.27)

In this Example, the fibers produced in Example 1 were placed in the buffer solution at 37° C. and pH=7.27, for different time intervals, mimicking the physiological, human body conditions. Prior to the buffer exposure, 12" fiber samples were kept under vacuum at room temperature for about three weeks.

After specific time spent in the buffer, portion of the fibers were removed and series of parameters were measured to estimate the hydrolyzing effect on the fibers in the first seven days of exposure: Length; Diameter; Straight Tensile Strength; and Knot Tensile Strength.

The summary of buffer hydrolysis data, specifically focusing on the parameters listed above is given in Tables 5A, 5B, 5C, and 5D below. As major Instron tensile property data (5C and 5D) indicate below, a significant degradation/hydrolysis occurred at day 7. For the purpose of this invention, a special attention is given to data points up to day 3, where the change of fiber properties is solely attributed to solvation into polymer matrix with no major effect of chemical hydrolysis.

TABLE 5-A

Fiber Length Measurements of 3-0 Monofilaments Described in Example 1 after exposed in buffered solution at 37° C. and pH = 7.27; Data represent averages from eight tests conducted

| Sample ID | 0 hours | 6 Hours | 24 Hours | 3 Days | 7 Days | % Length change @ day 3 |
|---|---|---|---|---|---|---|
| Sample 1-A | 12.15 | 11.87 | 11.72 | 11.73 | 11.92 | −3.5 |
| Sample 1-B | 11.95 | 11.84 | 11.98 | 12.00 | 12.10 | +0.4 |
| Sample 1-C | 11.91 | 11.82 | 11.85 | 11.86 | 12.01 | −0.4 |
| Sample 2 | 12.01 | 11.91 | 11.89 | 11.98 | 12.06 | −0.2 |
| Sample 3 | 11.65 | 7.27 | 7.85 | 8.00 | 7.45 | −31 |
| Sample 4 | 11.87 | 9.99 | 10.16 | 10.18 | 10.07 | −14 |

Data in Table 5A indicate practically no change in the length of the fiber for samples 1A, 1B, 1C, and 2. This suggests stable morphology, or sufficiently high level of crystallinity to prevent shrinkage of the fibers under physiological conditions up to 3 days. On the other hand, samples 3 and 4 showed measurable shrinkage induced by the buffer exposure, 31% and 14%, respectively.

Figure 6:
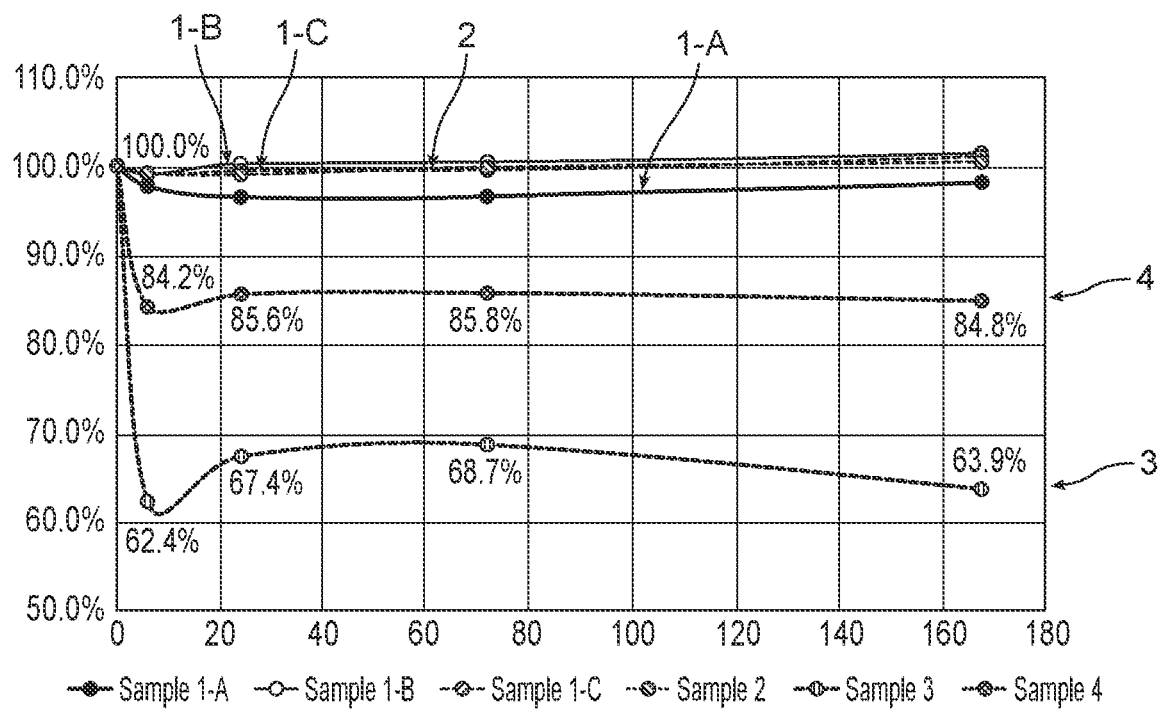
FIG. 6 shows data for suture length as a percentage of the original length over time (hours).

The same data is also presented as a chart in FIG. 6, showing data for suture length as a percentage of the original length over time (hours).

TABLE 5-B

Fiber Diameter Measurements of 3-0 Monofilaments Described in Example 1 after exposed in buffered solution at 37° C. and pH = 7.27; Data represent averages from eight tests conducted

| Sample ID | 0 hours | 6 Hours | 24 Hours | 3 Days | 7 Days | % diameter change @ day 3 |
|---|---|---|---|---|---|---|
| Sample 1-A | 11.43 | 11.50 | 11.56 | 11.54 | 11.65 | +0.96 |
| Sample 1-B | 11.39 | 11.48 | 11.44 | 11.39 | 11.45 | 0.00 |
| Sample 1-C | 11.36 | 11.45 | 11.43 | 11.41 | 11.50 | +0.44 |
| Sample 2 | 11.40 | 11.40 | 11.45 | 11.43 | 11.55 | +0.26 |
| Sample 3 | 11.59 | 14.66 | 13.95 | 13.79 | 13.30 | +19 |
| Sample 4 | 11.44 | 12.43 | 12.31 | 12.30 | 12.57 | +7.5 |

Changes in the fiber diameter presented in Table 5B show similar trend. While the diameter of samples 1A, 1B, 1C, and 2 stayed practically the same, those of samples 3 and 4 increased by 19% and 7.5%, respectively.

Figure 7:
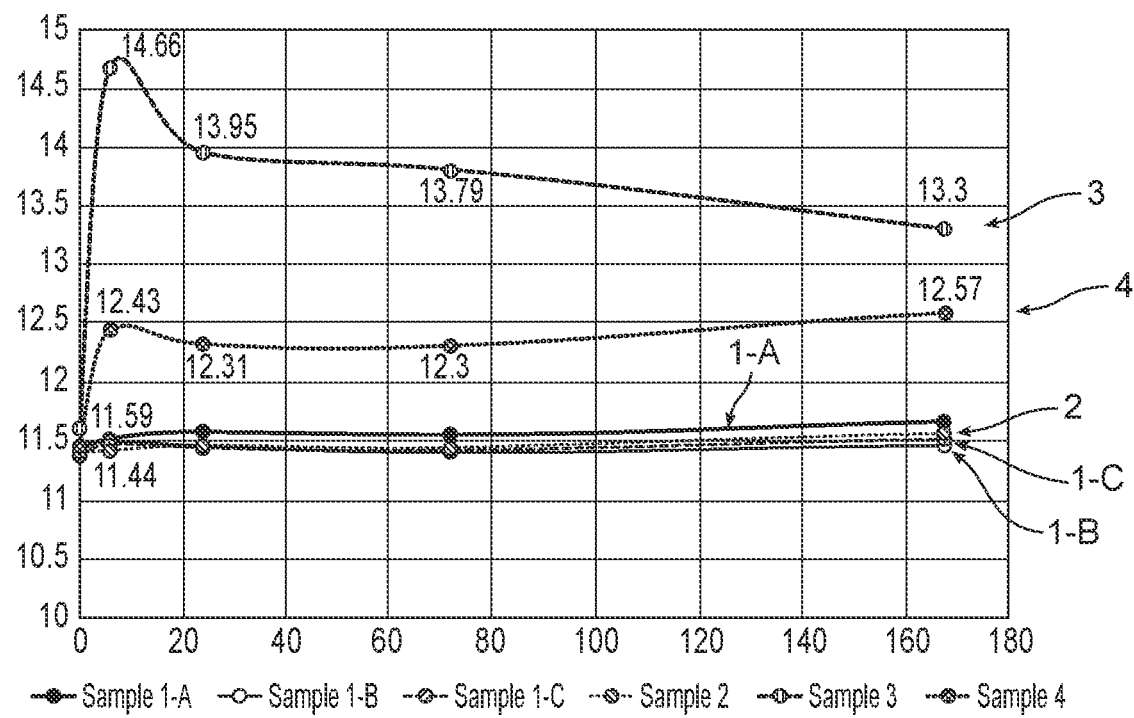
FIG. 7 shows data for suture diameter over time (hours)

The same data is also presented as a chart in FIG. 7, showing data for suture diameter over time (hours).

TABLE 5-C

Fiber Strength Measurements of 3-0 Monofilaments Described in Example 1 after exposed in buffered solution at 37° C. and pH = 7.27; Data represent averages from eight tests conducted

| Sample ID | 0 hours | 6 Hours | 24 Hours | 3 Days | 7 Days | % Strength change @ day 3 |
|---|---|---|---|---|---|---|
| Sample 1-A | 7.81 | 7.49 | 8.17 | 6.55 | 1.24 | −16 |
| Sample 1-B | 6.47 | 6.32 | 6.35 | 5.66 | 0 | −13 |
| Sample 1-C | 7.05 | 7.04 | 6.94 | 5.67 | 0.24 | −20 |
| Sample 2 | 7.33 | 7.70 | 7.44 | 6.34 | 0.18 | −14 |
| Sample 3 | 5.39 | 10.11 | 9.89 | 8.65 | 0 | +60 |
| Sample 4 | 6.09 | 9.10 | 8.49 | 8.94 | 0.42 | +47 |

Fiber Straight Strength data in Table 5C revealed a significant trend. For the higher crystallinity samples 1A, 1B, 1C, and 2, practically no change was observed in the first couple of days in the buffer. At day 3, a slight decrease in the strength (13-20%) was observed for these samples, potentially due to early onset of hydrolysis. Most unexpectedly, however, for the same time period samples 3 and 4 showed a dramatic jump in the fiber strength, 60% and 47%, respectively.

Figure 8:
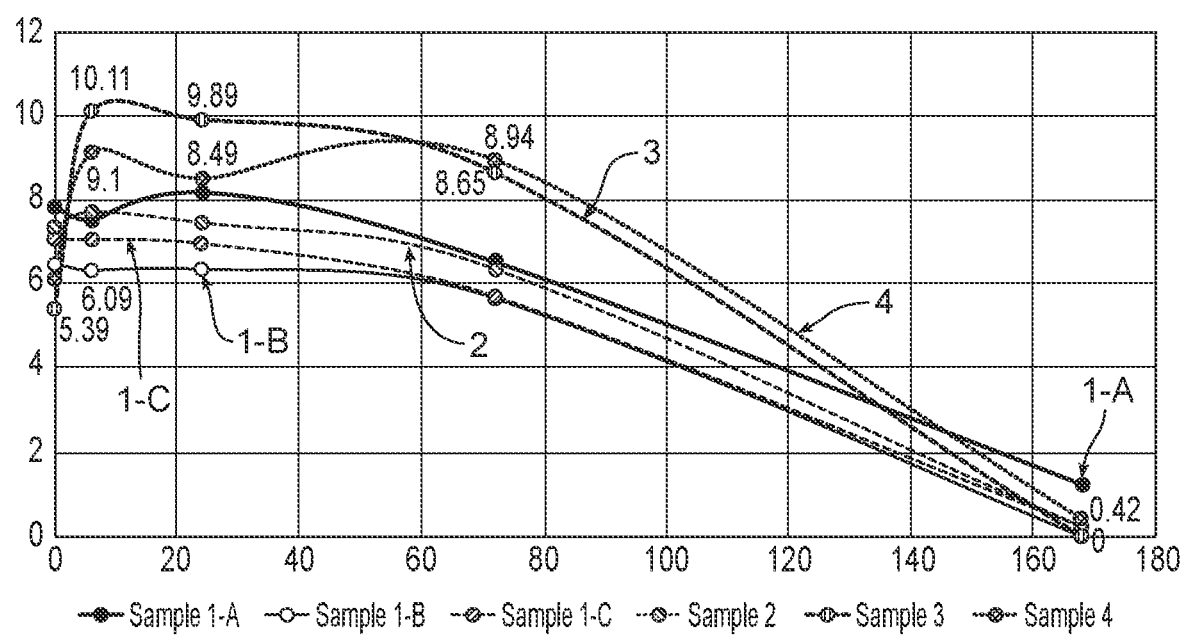
FIG. 8 shows data for suture strength over time (hours)

The same data is also presented as a chart in FIG. 8, showing data for fiber strength over time (hours).

TABLE 5-D

Fiber Knot Strength Measurements of 3-0 Monofilaments Described in Example 1 after exposed in buffered solution at 37° C. and pH = 7.27; Data represent averages from eight tests conducted

| Sample ID | 0 hours | 6 Hours | 24 Hours | 3 Days | 7 Days | % Knot change @ day 3 |
|---|---|---|---|---|---|---|
| Example 1-A | 1.38 | 1.51 | 1.93 | 1.50 | 0.47 | +8.7 |
| Example 1-B | 3.91 | 2.84 | 2.86 | 2.74 | 0 | −30 |
| Example 1-C | 2.46 | 2.07 | 2.49 | 2.01 | 0 | −18 |
| Example 2 | 2.08 | 2.41 | 2.12 | 1.81 | 0 | −13 |
| Example 3 | 4.47 | 8.01 | 9.44 | 7.54 | 0 | +69 |
| Example 4 | 3.10 | 4.23 | 4.17 | 4.85 | 0 | +56 |

Fiber Knot Strength data in Table 5D mimic the same unexpected behavior with the exclusion of sample 1A, which showed a small increased in the tensile knot strength at day 3 of about 9%. While the rest of higher crystallinity samples 1B, 1C, and 2 exhibit notable decrease in knot strength at day 3 (13-30%), the samples 3 and 4 showed opposite trend: huge improvements in knot strength of 69% and 56% was found, respectively.

Figure 9:
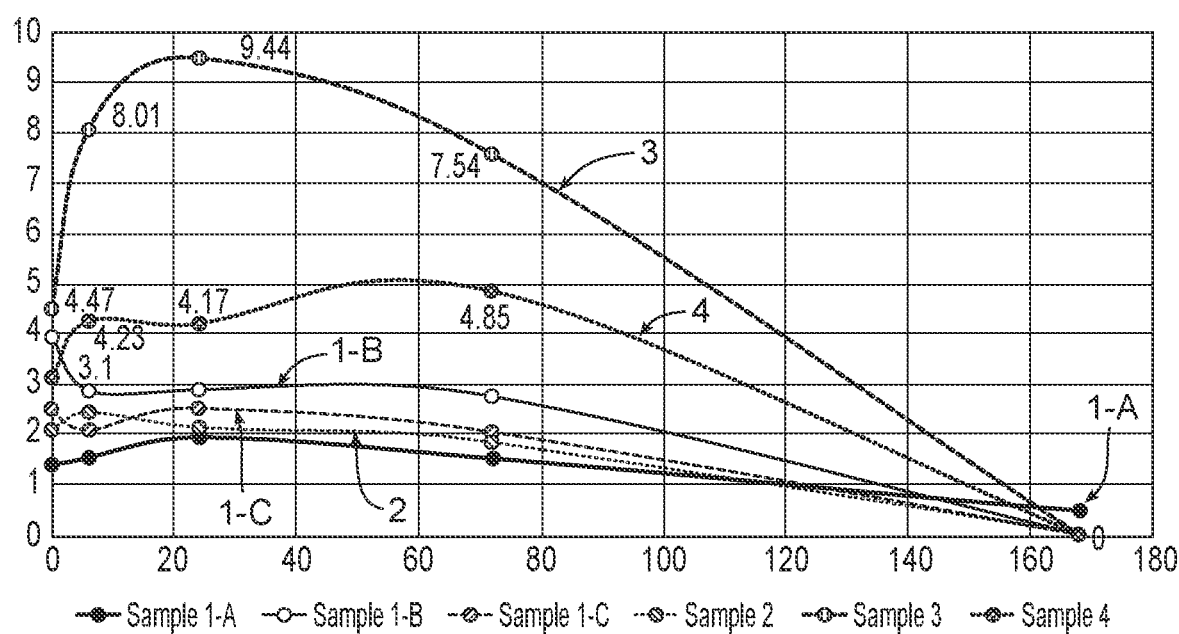
FIG. 9 shows data for suture knot strength over time (hours)

The same data is also presented as a chart in FIG. 9, showing data for Fiber Knot Strength over time (hours).

To summarize findings in Table 5A-D, the fiber samples with higher level of crystallinity 1A, 1B, 1C, and 2 behaved similarly to other conventional sutures. Their length, diameter, and major tensile properties seem not be affected by physiological buffer conditions at early stages of hydrolysis. These can be considered as non-inventive samples.

An amorphous fiber Example 3 was greatly affected by the exposure to physiological buffer conditions. Although dramatic improvement of tensile properties (straight strength and knot strength) was observed for this sample, too high shrinkage and extensive diameter increase prevent this sample to be useful in practical suture applications. In addition, "dry" oven data at 37° C. presented in Table 4 indicate stability, shelf-life concerns as significant fiber deformation was observed.

We found that the sample with limited crystallinity amount, Sample 4 showed optimal combination of properties suitable for practicing the art of this invention. After exposing this suture to physiological buffer solution study at 37° C. and pH=7.27 and prior to the time when significant hydrolysis starts to occur, this sample shrank to a desired level of about 15%, increased slightly in diameter between 5 to 10%, while its straight and knot strength values increases significantly by about 50%.

Below is an example of potential sutures currently on the market, in which the practicing the art of the present invention will not result in the desired properties being targeted by the present invention.

Example 5: Crystallization Properties of Polypropylene and Polyvinyl Difluoride (PVDF) Based Resin In this section, we will describe two polymer systems that cannot be used to practice the teachings of the present invention.

Polypropylene based sutures, such as PROLENE® Polypropylene Suture marketed by Ethicon Inc. have melting point around 165° C. Extruder's die temperature range for this type of polymers is between 192° C. and 218° C., recommended around 200° C. Based on internal extrusion process procedure for PROLENE® Suture (PS-0000028), for size 3-0 fibers, the orientation oven (Oven #1) recommended temperature range is 125° C.-145° C. (257° F.-293° F.), while the range for annealing/relaxation oven (Oven #2) is slightly higher, 135° C.-165° C. (275° F.-329° F.). In order to mimic crystallization behavior of the polymer during extrusion, we employed Differential Scanning Calorimetry (DSC) in the following manner.

Polypropylene resin sample was placed in the DSC apparatus and brought above its melting point to arise all crystals (200° C.). Then, the sample was quenched to minus (−)60° C. with, first by cooling it rapidly with the cooling rate of about 60° C./min. During the quench, the sample crystallized instantaneously at temperatures about 115° C. By conducting the subsequent heating scan at 10° C./min, we observed no additional crystallization, indicating that during this rapid quench the sample crystallized completely. In the second experiment, the polypropylene resin sample was quenched by placing the molten sample on the dry ice and held there (well below minus 60° C.) for a couple of minutes. By conducting the subsequent heating scan at 10° C./min, we again observed no additional crystallization, indicated that complete crystallization occurred during the dry ice quench. These set of experiments on polypropylene resin suggests that this polymer crystallize too fast to be useful for practicing art of this invention.

The resin formulation for PRONOVA® Poly (Hexafluoropropylene—VDF) Suture, also supplied by Ethicon Inc., is the blend consisting of roughly 50% polyvinylidene fluoride (PVDF) homopolymer and 50% of copolymer of 95% vinylidene fluoride and 5% of propylene hexafluoride. The other composition, 80/20 resin for PRONOVA Sutures, is composed of roughly 80% polyvinylidene fluoride (PVDF) homopolymer and 20% of copolymer of 95% vinylidene fluoride and 5% of propylene hexafluoride. For the purpose of this invention, we examined the crystallization properties of the first composition, 50/50 resin, which is expected to exhibit slower crystallization rate than the 80/20 formulation used primarily for smaller suture sizes. We repeated the DSC melting and quenching steps as described in previous paragraph for polypropylene. After examination of the DSC second heating scan for 50/50 resin, we observed no additional crystallization in the thermograph. The sample, again, crystallized extremely rapidly during the quench (around 130° C.), leaving no amorphous part for the second heating scan.

In addition, we conducted a Melt Index apparatus test, during which we produced a fiber extrudate from 50/50 resin, and instantaneously drawn two, four or seven times from its original length. As a control, we tested non-drawn sample, as well. Pieces of drawn and non-drawn fibers were immediately put on a dry ice to quench the samples below (−) minus 60° C. for five minutes. Subsequent DSC heating scans at 10° C./min revealed no crystallization for all samples tested. The glass transition temperatures were around minus (−) 33° C., melting points around 172° C., with the heat of fusion for all samples around 55 J/g, values very close to those of the first heating scans for 50/50 resin. This set of measurements indicate that crystallization rate of this polymer is too high for the resin to be used in practicing art of the present invention.

However, non-absorbable sutures ETHIBOND® Extra Polyester Suture and NUROLON® Nylon Suture made from Nylon 6 and Nylon 6,6 polymers, respectively fit profiles to be very good candidates for practicing art of this invention. Their fiber glass transition temperature fall in the range 40° C. to 50° C., with superb water absorption rate post-implantation. Nylon 6 polymer showed less crystallinity and slower crystallization rate than Nylon 6,6 counterpart.

The field of this invention is a semi-crystalline synthetic suture made from absorbable or non-absorbable polymer having glass transition temperatures between 40° C. and 55° C. exhibiting a limited crystallinity level between 10% and 25%. Ideally, polymers need to display slow enough crystallization kinetics during monofilament or multifilament extrusion to allow for precise control the crystallinity level of resulting fibers. Data in this study indicate that 90/10 Gly/Lac monofilament showed 14% decrease in fiber length and 8% increase in the fiber diameter after exposure to physiological body conditions. The inventive, leading 90/10 Gly/Lac composition exhibits crystallinity level of about 15% and showed significant increase in tensile straight and knot strength of about 50% after exposure to physiological, body conditions prior major hydrolysis occurred.

Advantageously, the inventive sutures exhibit surprising properties, including: Suture shrinkage for about 10 to 15% in a body post-implantation to adjust for decrease in swelling of surrounding tissues; Suture's diameter increases for about 5 to 10% in a body post-implantation, allowing to close the gap between holes made by the difference in needle and suture diameters; Major suture tensile properties, such as straight and knot strength increase significantly by about 50% in a body post-implantation prior to major hydrolysis occurred; and Suture crystallization/morphology is controlled by extrusion processing parameters with no chemical composition change.

Although this invention has been shown and described with respect to detailed embodiments thereof, it will be understood by those skilled in the art that various changes in form and detail thereof may be made without departing from the spirit and scope of the claimed invention.

We claim:

1. A length adaptive surgical suture comprising a monofilament or a braid of a plurality of filaments, the suture having an original length when implanted and a second length that is 2%-20% longer than the original length within a first twenty-four (24) hour period of time after implantation to accommodate tissue swelling, said suture held by a soluble constricting element in a shortened or constricted state at the original length prior to implantation,
   wherein elongating of the suture is caused by a dissolution of the constricting element within 24 hours upon exposure to body fluids and tissues.

2. The suture of claim 1 comprising the braid of the plurality of filaments, wherein the soluble constricting element comprises a constricting yarn holding the braid in the constricted state at the original length that is shorter than the second length, wherein such constricting yarn dissolves upon exposure to body fluids and tissue.

3. The suture of claim 1 comprising the braid of the plurality of filaments, wherein the soluble constricting element comprises a constricting yarn forming a core of the braid and holding the braid in the constricted or shortened state, wherein said constricting yarn dissolves upon exposure to body fluids.

4. A length adaptive surgical suture comprising a monofilament or a braid of a plurality of monofilaments, the suture having an original length when implanted and a second length that is shorter from the original length wherein at least some of the monofilaments in the suture are a semi-crystalline polymer having a glass transition temperature between 40° C. and 55° C. and exhibiting a crystallinity level between 10% and 25%.

5. The suture of claim 4 wherein said second length is at least 10% less than the original length post-implantation.

6. The suture of claim 1 or 4 wherein each monofilament has a diameter that increases between 5% and 10% in a body post-implantation.

7. The suture of claim 1 or 4 wherein have a suture tensile strength and a knot strength that each increase by at least about 20% in a body post-implantation prior to a major degradation and hydrolysis of said suture.

8. An adaptive surgical suture, comprising a semi-crystalline absorbable synthetic polymer made from glycolide and lactide copolymer having an original length, a glass transition temperature in between 40° C. and 45° C. and a crystallinity level of about 15%,
   wherein said suture has a second length that decreases about 15% post-implantation and a diameter that increases about 10% in a body post-implantation and wherein said suture tensile strength and knot strength increase by at least about 40% in a body post-implantation prior to a major degradation and hydrolysis of said suture.

9. A length adaptive surgical suture comprising a monofilament or a braid of a plurality of monofilaments, the suture having an original length when implanted and a second length that is greater within the first twenty-four (24) hour period after implantation to accommodate tissue swelling,
   the suture held by a soluble constricting element in a shortened or constricted state at the original length prior to implantation, wherein elongating of the suture is caused by a dissolution of the constricting element within 24 hours upon exposure to body fluids and tissues;
   the suture having a third length thereafter that is less than the original length to tighten the tissue holding as the tissue heals.

10. The length adaptive surgical suture of claim 9, wherein the suture comprises a semi-crystalline polymer having glass transition temperature in between 40° C. and 55° C. and exhibiting a crystallinity level between 10% and 25%, wherein a crystallization of said semi-crystalline polymer causes said suture thereafter to contract, shortening said suture to the third length.

\* \* \* \* \*